(12) United States Patent
Wooley

(10) Patent No.: US 7,992,568 B2
(45) Date of Patent: *Aug. 9, 2011

(54) INTEGRATED OPERATING ROOM SHEET SYSTEM AND METHOD FOR USING THE SAME

(75) Inventor: Deborah M. Wooley, Birmingham, AL (US)

(73) Assignee: Microtek Medical, Inc., St. Paul, MN (US)

( * ) Notice: Subject to any disclaimer, the term of this patent is extended or adjusted under 35 U.S.C. 154(b) by 142 days.

This patent is subject to a terminal disclaimer.

(21) Appl. No.: 12/556,769

(22) Filed: Sep. 10, 2009

(65) Prior Publication Data

US 2009/0320857 A1    Dec. 31, 2009

Related U.S. Application Data

(63) Continuation of application No. 10/839,372, filed on May 5, 2004, now Pat. No. 7,604,007.

(60) Provisional application No. 60/468,186, filed on May 5, 2003, provisional application No. 60/530,533, filed on Dec. 17, 2003.

(51) Int. Cl.
 *A61B 19/00* (2006.01)

(52) U.S. Cl. ........................................ 128/849; 128/855

(58) Field of Classification Search .......... 128/849–852, 128/854–855; 5/621–624
 See application file for complete search history.

(56) References Cited

U.S. PATENT DOCUMENTS

| | | | |
|---|---|---|---|
| 3,537,446 A | 11/1970 | Wright et al. | |
| 3,674,613 A | 7/1972 | Lavigne | |
| 3,693,618 A | 9/1972 | Madden | |
| 3,707,964 A | 1/1973 | Patience et al. | |
| 3,791,381 A | 2/1974 | Krzewinski | |
| 3,835,851 A | 9/1974 | Villari | |
| 3,856,006 A | 12/1974 | Krzewinski | |
| 3,916,447 A | 11/1975 | Thompson | |
| 4,051,845 A | 10/1977 | Collins | |
| 4,164,941 A | 8/1979 | Knopick et al. | |
| 4,397,309 A | 8/1983 | McAllester | |
| 4,457,026 A | 7/1984 | Morris | |
| 4,586,498 A | 5/1986 | Morris | |
| 5,133,097 A | 7/1992 | Pyles | |
| 5,148,558 A | 9/1992 | Dunn | |
| 5,151,314 A | 9/1992 | Brown | |
| 5,291,903 A | 3/1994 | Reeves | |
| 5,503,163 A | 4/1996 | Boyd | |
| 5,515,868 A | 5/1996 | Mills | |
| 5,640,975 A | 6/1997 | Diao | |
| 5,733,629 A | 3/1998 | Insley | |
| 5,921,242 A | 7/1999 | Newman | |
| 6,314,958 B1 | 11/2001 | Harroll et al. | |
| 6,564,803 B2 | 5/2003 | Lofgren | |
| 6,767,553 B2 | 7/2004 | Sun | |

OTHER PUBLICATIONS

Engineering Change Order dated Jul. 6, 2005.
http://web.archive.org/web/20011201213602/www.cleanop.com/comain.htm.
http://web.archive.org/web/20020305231337/www.cleanop.com/comain.htm.
Products advertized on the website http://web.archive.org/web/20011130233047/http://cleanop.com/.
The 2002 CleanOpTM System (i.e., a drape combination system comprising an operating room table sheet, a lift sheet, one or more optional arm board covers, and an optional head first sold in Apr. 2002).

*Primary Examiner* — Patricia M Bianco
*Assistant Examiner* — Camtu T Nguyen
(74) *Attorney, Agent, or Firm* — Andrew D. Sorensen; Laura C. Dilorenzo

(57) ABSTRACT

Disposable operating room surgical draping systems are disclosed. Methods of using disposable operating room surgical draping systems are also disclosed.

13 Claims, 10 Drawing Sheets

INTEGRATED OPERATING ROOM SHEET SYSTEM AND METHOD FOR USING THE SAME

CROSS-REFERENCE TO RELATED APPLICATIONS

This application is a continuation application of U.S. application Ser. No. 10/839,372, filed May 5, 2004, now allowed which claims priority to U.S. Provisional Application Ser. Nos. 60/468,186, filed May 5, 2003 and 60/530,533, filed Dec. 17, 2003. The entire disclosures of which are hereby expressly incorporated herein by reference including, without limitation, the specification, claims, and abstracts, as well as any figures, tables, or drawings thereof.

FIELD OF THE INVENTION

The present invention relates generally to disposable operating room surgical draping systems, and methods for using disposable operating room surgical draping systems in an operating room setting.

BACKGROUND OF THE INVENTION

Hospital operating rooms often utilize disposable drapes and linens. In an effort to save time and provide convenience, some hospitals utilize an operating room kit that contains drapes, linens and other disposable products that might be used during a given procedure including, but not limited to, a variety of bags, disposable wipes, abdominal safety straps, blood solidification systems, suction tubing, and disposable mop heads. Such kits are commonly referred to operating room decontamination setup supplies or "room turnover" supplies.

In some cases, such kits may contain numerous drapes or linens that need to be placed on or near an operating table in a particular order. However, some hospital personnel may be unfamiliar with the particular order in which the drapes should be placed or, alternatively, those that are aware of the order in which the drapes should be placed, may find it time consuming to do so. What complicates matters for hospital personnel is that the numerous drapes or linens of the kits are separately folded components. For example, the kit might contain an operating room table sheet folded independently from a lift sheet. The hospital personnel must independently unfold each drape or linen and properly place the drape or linen over components of the operating room table in a particular order to minimize the probability of contamination or cross-contamination of the operating room setting.

What is needed in the art is a disposable operating room surgical draping system and a method of using such a system so as to (i) minimize the time necessary to properly prepare an operating table prior to use, (ii) minimize the decision-making needed by hospital personnel in order to properly equip the operating table setting, or (iii) both (i) and (ii).

SUMMARY OF THE INVENTION

The present invention is directed to a disposable operating room surgical draping system suitable for use in an operating room setting. The disposable operating room surgical draping system of the present invention addresses one or more of the above-mentioned deficiencies in the art. In particular, the disposable operating room surgical draping system of the present invention enables hospital personnel to efficiently and effectively prepare an operating table setting prior to use.

According to one exemplary embodiment of the present invention, the disposable operating room surgical draping system comprises operating room table sheet nested, and a lift sheet nested within the operating room table sheet such that when the operating room table sheet is unfolded on an operating room table, the lift sheet and operating room table sheet are automatically arranged in the correct order and orientation. The operating room surgical draping system may further include other items nested within the operating room table sheet including, but not limited to, one or more arm board covers, at least one headrest cover, and combinations thereof.

In a further exemplary embodiment of the present invention, the disposable operating room surgical draping system comprises an operating room table sheet, and one or more components in combination with the operating room table sheet, wherein the one or more components are nested within the operating room table sheet when the operating room table sheet is in a folded configuration. In this embodiment, the one or more components may comprise a lift sheet, at least one arm board cover, at least one head rest cover, other "room turnover" supplies, or any combination thereof.

The disposable operating room surgical draping system of the present invention provides numerous technical advantages. For example, in one embodiment of the present invention, an operating room surgical draping system is provided that facilitates the placing of surgical drapes on an operating table in the correct order and reduces the time associated with unfolding individual drapes provided in a multiple drape/linen kit. This allows a person unfamiliar with the particular drapes to properly set up the operating room. It also reduces the time commitment of personnel needed to properly set up an operating room.

One such exemplary disposable operating room surgical draping system of the present invention comprises a one-piece surgical drape for use on an operating room table. The exemplary one-piece surgical drape of the present invention may comprise a table sheet, a pair of integrated wings attached to the table sheet wherein each integrated wing is adapted to protect respective arm boards of the operating table, and a pair of straps each attached to respective wings for secure attachment of a patient's arm to the arm boards.

In another exemplary embodiment of the present invention, the disposable operating room surgical draping system comprises an operating room table sheet, wherein the operating room table sheet has a cuff at one end and on a lower surface of the operating room table sheet. The cuff may be sized so as to be capable of partially enclosing a portion of an operating room table mattress on an operating room table.

In yet a further exemplary embodiment of the present invention, the disposable operating room surgical draping system comprises an operating room table sheet, wherein the operating room table sheet has a cuff at a first end and on a lower surface of the operating room table sheet, wherein the cuff is sized so as to be capable of partially enclosing a portion of an operating room table mattress; a lift sheet attached to an upper surface of the operating room table sheet; two arm board covers attached to an upper surface of the operating room table sheet, each of the arm board covers having strap components attached thereto so that ends of the strap components are releasably attachable to one another; a head rest cover attached to an upper surface of the operating room table sheet at the first end of the operating room table sheet; and two separate panels attached to opposite sides of an upper surface of the operating room table sheet, wherein each panel is capable of extending from an operating room table to an operating room floor positioned beneath the operating room table.

The present invention is further directed to methods of preparing an operating room table for a surgical procedure. In one exemplary embodiment of the present invention, the method of preparing an operating room table comprises the steps of: placing any of the above-described disposable operating room surgical draping systems onto an upper surface of the operating room table; removing a kit lining or packaging material from the disposable operating room surgical draping system if present; and unfolding the disposable operating room surgical draping system. The exemplary method may include a number of additional steps including, but not limited to, unfolding one or more panels, when present, as needed to extend the one or more panels a distance toward an operating room floor; placing the at least one head rest cover over a head resting component if present; placing the at least one arm board cover over an arm board of the operating room table if present; unfolding the lift sheet as needed; and positioning one end of the disposable operating room surgical draping system so that the cuff of the disposable operating room surgical draping system, when present, fits over a portion of an operating room table mattress.

These and other features and advantages of the present invention will become apparent after a review of the following detailed description of the disclosed embodiments and the appended claims.

BRIEF DESCRIPTION OF THE FIGURES

The present invention is further described with reference to the appended figures, wherein.

DETAILED DESCRIPTION OF THE INVENTION

The present invention is directed to disposable operating room surgical draping systems for use in an operating room setting. The present invention is further directed to methods of using disposable operating room surgical draping systems to properly prepare an operating table prior to exposing the table to a patient. In addition, the present invention is directed to systems and procedures for efficiently equipping an operating table prior to use so as to minimize the amount of time necessary to properly prepare the operating table prior to exposing the table to a patient.

In one embodiment of the present invention, the disposable operating room surgical draping system comprises an operating room table sheet, and one or more components in combination with the operating room table sheet, wherein the one or more components are nested within the operating room table sheet when the operating room table sheet is in a folded configuration. The one or more components may include, but are not limited to, at least one lift sheet, at least one arm board cover, and at least one head rest cover. In one desired embodiment of the present invention, the one or more components include a single lift sheet, two separate arm board covers, and a single head rest cover. One exemplary disposable operating room surgical draping system is shown in FIG. 1.

Figure 1:
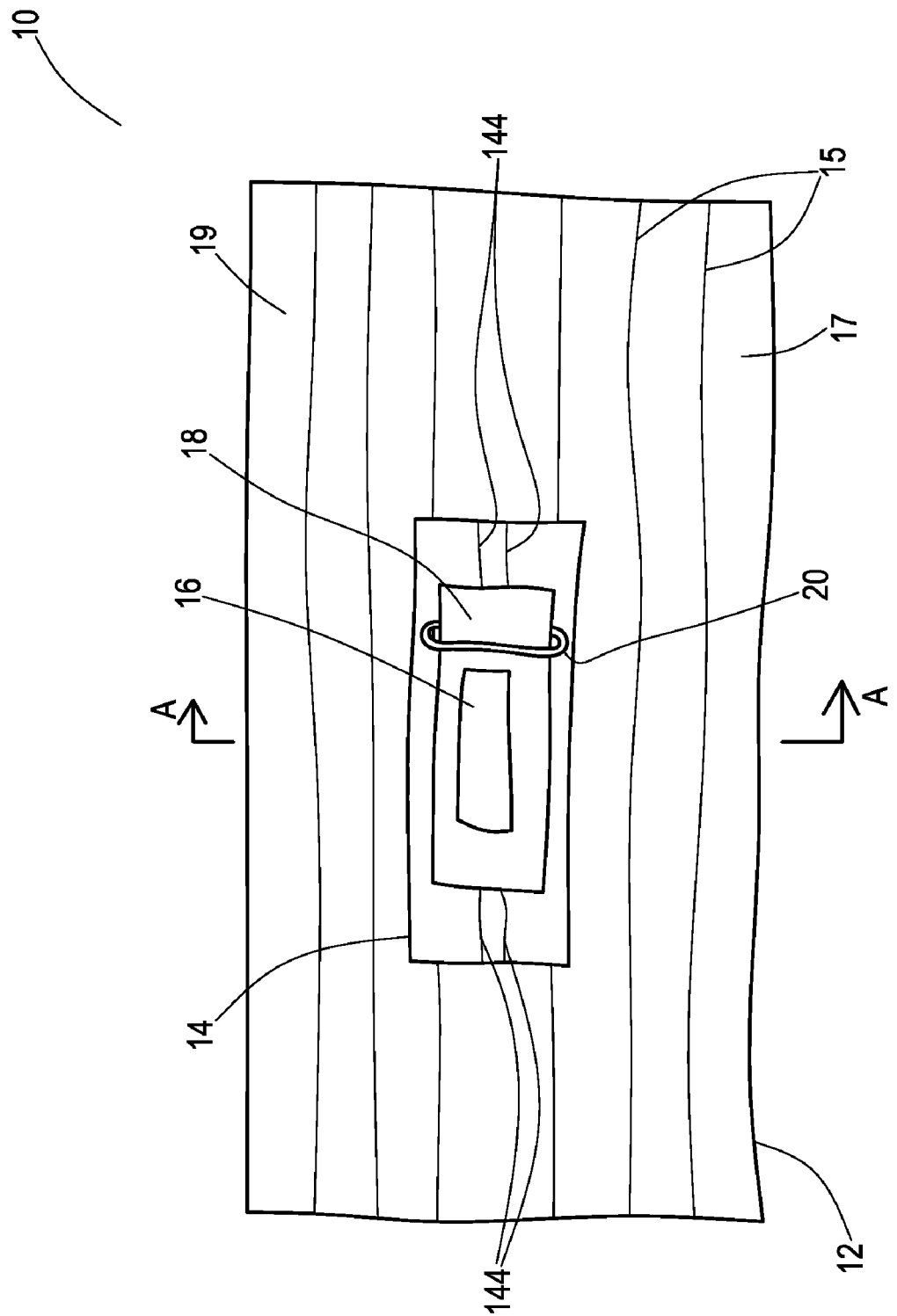
FIG. 1 depicts a top view of an exemplary disposable operating room surgical draping system of the present invention.

As shown in FIG. 1, exemplary disposable operating room surgical draping system 10 comprises operating room table sheet 12, fan-folded lift sheet 14, arm board cover 18, head rest cover 16, and arm board strap 20 positioned around a portion of arm board cover 18. Although not shown in FIG. 1, the disposable operating room surgical draping system may further comprise additional components including, but not limited to, one or more panels attached to the operating room table sheet wherein the one or more panels, when fully extended, extend a length substantially equal to a distance from an operating room table to a floor of an operating room, a cuff on a lower surface of the operating room table sheet wherein the cuff is sized so as to partially enclose a portion of an operating room table mattress on an operating room table, one or more other "room turnover" components (i.e., a variety of bags, disposable wipes, abdominal safety straps, blood solidification systems, suction tubing, and disposable mop heads), and combinations thereof.

As described above, the disposable operating room surgical draping system of the present invention may comprise a number of components. A description of some of the suitable exemplary components is provided below.

I. Disposable Operating Room Surgical Draping System Components

The disposable operating room surgical draping system of the present invention may comprise, but are not limited to, one or more of the following components.

A. Operating Room Table Sheet

The disposable operating room surgical draping system of the present invention comprises an operating room table sheet such as exemplary operating room table sheet 12 shown in FIG. 1. Typically, the operating room table sheet comprises a multi-layer article comprising a liquid impervious layer, and a fiber-containing layer adjacent to the liquid impervious layer. The liquid impervious layer may comprise a polymeric film-forming material, such as polyethylene, and typically has an average layer thickness of less than about 50 microns (μm) (about 2 mil). Desirably, the polymeric film-forming material comprises a material having a relatively high coefficient of friction or degree of tackiness so that the operating room table sheet does not slip off of the operating room table mattress during use. One desired polymeric film-forming material having a relatively high coefficient of friction comprises polyethylene.

The fiber-containing layer may comprise a woven or nonwoven fabric layer, or may comprise a layer of fibers adjacent to the liquid impervious layer. The fibers of the fiber-containing layer may comprise a polymeric film-forming material, such as polypropylene, and typically has an average layer thickness of less than about 250 microns (μm) (about 10 mil). In one desired embodiment of the present invention, the fiber-containing layer comprises a polypropylene spunbonded fabric layer having a basis weight of about 1 ounce per square yard.

Although a two-layered construction as described above may be used in the present invention, in other embodiments, a three or four layered construction may be used wherein at least one layer containing superabsorbent material or particles (SAP) is interposed between the above-described liquid impervious layer and the above-described fiber-containing layer. The SAP-containing layer or layers may further comprise additional components such as fibrous materials (e.g., pulp fibers, synthetic fibers, or a combination thereof), filler materials, or a combination thereof.

The SAP-containing layer or layers may each comprise a substantially uniform distribution of superabsorbent material or particles across an area of the operating room table sheet, or alternatively, may comprise a non-uniform distribution of superabsorbent material or particles across an area of the operating room table sheet. For example, an operating room table sheet of the present invention may have a layer of superabsorbent material or particles within a central location of the operating room table sheet (e.g., an area positioned directly above the operating table mattress), but be substantially free of superabsorbent material or particles in an outer periphery of the operating room table sheet.

Any known superabsorbent material may be used in the operating room table sheet of the present invention. Suitable commercially available superabsorbent materials include, but are not limited to, superabsorbent materials available from Stockhausen (Greensboro, N.C.) and Dow Chemical (Midland, Mich.).

In a further embodiment of the present invention, the operating room table sheet of the present invention comprises an outermost fiber-containing layer as described above, a mesh structure, a layer containing superabsorbent material or particles, and a lower layer of liquid impervious material as described above, wherein the mesh structure provide additional tear strength to the operating room table sheet.

In yet a further embodiment of the present invention, the operating room table sheet comprises a cuff on a lower surface of the operating room table sheet. The cuff forms a "pocket" on the lower side of the operating room table sheet. The cuff or pocket is sized so as to fit over at least a portion of an operating room table mattress positioned on an operating room table. The cuff may be any size such that the cuff fits over an operating room table mattress. In one embodiment of the present invention, the cuff has a width (i.e., across the operating room table sheet) of about 24 inches and a length (i.e., along the length of the operating room table sheet) of about 6 inches.

The cuff feature of the operating room table sheet or drape enables a single person to quickly and properly cover an operating room table mattress. In an exemplary method, a person secures the cuff of the sheet or drape over the mattress to stabilize the sheet or drape. Then, the person pulls the fan-folded disposable operating room surgical draping system from head to foot to cover the operating room table.

Operating room table sheets used in the present invention typically have dimensions so that the operating room table sheet completely covers an upper surface of an operating room table mattress. In one exemplary embodiment of the present invention, the operating room table sheet has a width ranging from about 24 to about 60 inches, and a length ranging from about 72 to about 104 inches. In one desired embodiment, the operating room table sheet has a width of about 44 inches, and a length of about 92 inches. In a further desired embodiment, the operating room table sheet has a width of about 42 inches, and a length of about 87 inches.

B. Lift Sheet

The disposable operating room equipment assembly of the present invention further comprises at least one lift sheet such as exemplary lift sheet 14 shown in FIG. 1. The lift sheet is designed to assist in the transfer of a patient onto an operating room mattress, as well as to position a patient's arms during a surgical procedure. For example, the lift sheet may be used to "tuck" the arms by a patient's side to temporarily restrain the patient's arms. Moreover, the lift sheet may be used to separate a patient's arm from the patient's body if the patient's arm is the focus of attention. Lift sheets are commonly referred to in the art as "transfer sheets" and "draw sheets."

Typically, the lift sheet comprises a nonwoven or woven fabric layer. The nonwoven fabric layer may comprise a spunbonded fabric layer, spunlaced fabric layer, or any other nonwoven fabric layer. The fibers of the nonwoven fabric layer may comprise a polymeric film-forming material, such as polyvinyl alcohol, and typically has an average layer thickness of less than about 500 microns (μm) (about 20 mil). In one desired embodiment of the present invention, the lift sheet comprises a cross-lapped, spunlaced nonwoven fabric layer of polyvinyl alcohol fibers having a basis weight of about 70 grams per square meter.

Lift sheets used in the present invention may have a variety of dimensions. Typically, the lift sheet has a width ranging from about 24 to about 50 inches, and a length ranging from about 48 to about 92 inches. In one desired embodiment, the lift sheet has a width of about 35 inches, and a length of about 65 inches. In a further desired embodiment, the lift sheet has a width of about 39 inches, and a length of about 77 inches.

In one embodiment of the present invention, the lift sheet comprises a butterfly lift sheet comprising two similarly sized lift sheets tacked to one another along a central portion of the lift sheets and running lengthwise along the lift sheets. In such an embodiment, the butterfly lift sheet may be used to transfer a patient onto an operating room table, and then arms of the patient may be separated from the patient's body by positioning the patient's arms between upper and lower portions of the butterfly lift sheet.

C. Arm Board Covers

The disposable operating room surgical draping system of the present invention may further comprise one or more arm board covers or "wings" such as exemplary arm board cover 18 shown in FIG. 1. Typically, arm board covers used in the present invention comprise a multi-layer material comprising a liquid impervious layer, and a fiber-containing layer adjacent to the liquid impervious layer similar to the materials used to form the above-described operating room table sheet; however, additional layers may also be present such as a layer containing superabsorbent material as described above. The liquid impervious layer may comprise a polymeric film-forming material, such as polyethylene, and typically has an average layer thickness of less than about 50 microns ($\mu$m) (about 2 mil). The fiber-containing layer may comprise a woven or nonwoven fabric layer, or may comprise a layer of fibers. The fibers of the fiber-containing layer may comprise a polymeric film-forming material, such as polypropylene, and typically has an average layer thickness of less than about 250 microns ($\mu$m) (about 10 mil).

In one desired embodiment of the present invention, the arm board covers or "wings" comprise a tubular structure formed from the above-described multi-layer material, wherein the liquid impervious layer forms an inner surface of the tubular structure, and the fiber-containing layer forms an outer layer of the tubular structure. In this embodiment, the arm board cover may be opened (i.e., the tubular cavity is expanded), and then positioned over and around an arm board of an operating room table.

Straps may be used to (i) secure the arm board cover over and onto the arm board of an operating room table, (ii) secure a patient's arm to the covered arm board, or (iii) both (i) and (ii). Straps may be connected to or separate from the arm board covers or "wings" used in the present invention. Suitable strap materials include, but are not limited to, elastic materials, and fabric strips. Desirably, the strap materials comprise elastic materials. In addition, the strap materials may further comprise one or more fasteners attached to one or more ends of the straps. Suitable fasteners include, but are not limited to, hook-and-loop fasteners, and double-sided pressure-sensitive adhesive tapes. Such fasteners may be used to releasably attach to another surface including, but not limited to, one end of a given strap to an arm board cover, an opposite end of the strap, or some other portion of the strap.

In a further desired embodiment of the present invention, the arm board covers or "wings" comprise a flat structure formed from the above-described multi-layer material, wherein the liquid impervious layer forms a lower surface of the arm board cover, and the fiber-containing layer forms an upper surface of the arm board cover. In this embodiment, the arm board cover is positioned over an arm board of an operating room table so that the lower surface of the arm board cover (i.e., the liquid impervious layer) is adjacent to the arm board.

The arm board covers or "wings" having a flat structure may also further comprise one or more straps as described above. Typically, a set of corresponding straps are positioned on either side of the arm board cover having a flat structure. The set of corresponding straps is typically used to secure the arm board cover to an arm board of an operating room table. Fasteners, such as those described above, may be used to releasably attach one end of a strap to a portion of a corresponding strap or to another surface.

Arm board covers or "wings" used in the present invention typically have dimensions so that the arm board cover or "wing" completely covers an upper surface of an arm board used in combination with an operating room table. In one exemplary embodiment of the present invention, the arm board cover has a width ranging from about 6 inches to about 36 inches, and a length ranging from about 24 inches to about 48 inches. In one desired embodiment wherein the arm board cover has a tubular structure, the arm board cover has a width of about 13 inches, and a length of about 31 inches. In a further desired embodiment wherein the arm board cover has a flat structure, the arm board cover has a width of about 19 inches, and a length of about 35 inches.

Straps suitable for use with the arm board covers typically have a strap width of about 2 inches and a length ranging from about 10 inches to about 45 inches. In one desired embodiment wherein the strap is not connected to the arm board cover, the strap has a strap width of about 2 inches and a length of about 30 inches. In one desired embodiment wherein a set of corresponding straps are connected to the arm board cover, each strap in the set has a strap width of about 2 inches and a length of about 18 inches.

In one desired embodiment of the present invention, the disposable operating room surgical draping system comprises two separate tubular arm board covers, each of which further comprises straps surrounding a tubular portion of each arm board cover. In this embodiment, the straps are not connected to the tubular arm board covers, but surround the tubular arm board covers once the tubular arm board covers are placed over arm boards associated with an operating room table.

Any of the above-described arm board covers may further comprise one or more of the above-described fasteners on an outer surface of the arm board cover in order to releasably attach the arm board cover to the operating room table sheet of the surgical draping system. In one desired embodiment, each arm board cover of the surgical draping system comprises at least one fastener in the form of a double-sided adhesive tape so that the arm board covers may be attached to and repositioned as needed along an outer surface of the operating room table sheet or any other component of the surgical draping system.

D. Head Rest Covers

The disposable operating room surgical draping system of the present invention may further comprise one or more head rest covers such as exemplary head rest cover 16 shown in FIG. 1. Typically, head rest covers used in the present invention comprise a multi-layer material comprising a liquid impervious layer, and a fiber-containing layer adjacent to the liquid impervious layer similar to the materials used to form the operating room table sheet and the arm board covers. The liquid impervious layer may comprise a polymeric film-forming material, such as polyethylene, and typically has an average layer thickness of less than about 50 microns ($\mu$m) (about 2 mil). The fiber-containing layer may comprise a woven or nonwoven fabric layer, or may comprise a layer of fibers. The fibers of the fiber-containing layer may comprise a polymeric film-forming material, such as polypropylene, and typically has an average layer thickness of less than about 250 microns ($\mu$m) (about 10 mil).

In one desired embodiment of the present invention, the head rest cover comprises a tubular structure formed from the above-described multi-layer material, wherein the liquid impervious layer forms an inner surface of the tubular structure, and the fiber-containing layer forms an outer layer of the tubular structure. In this embodiment, the head rest cover may be opened (i.e., the tubular cavity is expanded), and then positioned over and around a head positioning article, such as a pillow or deformable foam.

The tubular structure may further comprise a cuff on a lower surface of the head rest cover, similar to the above-described cuff on the operating room table sheet. The cuff forms a "pocket" on the lower side of the head rest cover. The cuff or pocket is sized so as to fit over at least a portion of an operating room table mattress positioned on an operating room table. In one embodiment of the present invention, the cuff has a width that equals the width of the head rest cover (e.g., about 14 inches) and a length (i.e., along the length of the head rest cover) of about 4 inches.

In a further desired embodiment of the present invention, the head rest cover comprise a flat structure formed from the above-described multi-layer material, wherein the liquid impervious layer forms a lower surface of the head rest cover, and the fiber-containing layer forms an upper surface of the head rest cover. In this embodiment, the head rest cover is positioned over a head positioning article on an operating room table so that the lower surface of the head rest cover (i.e., the liquid impervious layer) is adjacent to the head positioning article.

Head rest covers used in the present invention typically have dimensions so that the head rest cover completely covers an upper surface of a head positioning article used in combination with an operating room table. In one exemplary embodiment of the present invention, the head rest cover has a width ranging from about 10 inches to about 36 inches, and a length ranging from about 10 inches to about 36 inches. In one desired embodiment wherein the head rest cover has a tubular structure, the head rest cover has a width of about 14 inches, and a length of about 15 inches. In a further desired embodiment wherein the head rest cover has a flat structure, the head rest cover has a width of about 25 inches, and a length of about 19 inches.

Typically, a given disposable operating room surgical draping system of the present invention comprises a single head rest cover. In one desired embodiment of the present invention, the disposable operating room surgical draping system of the present invention comprises a single, tubular head rest cover as described above.

E. Panels

Figure 11:
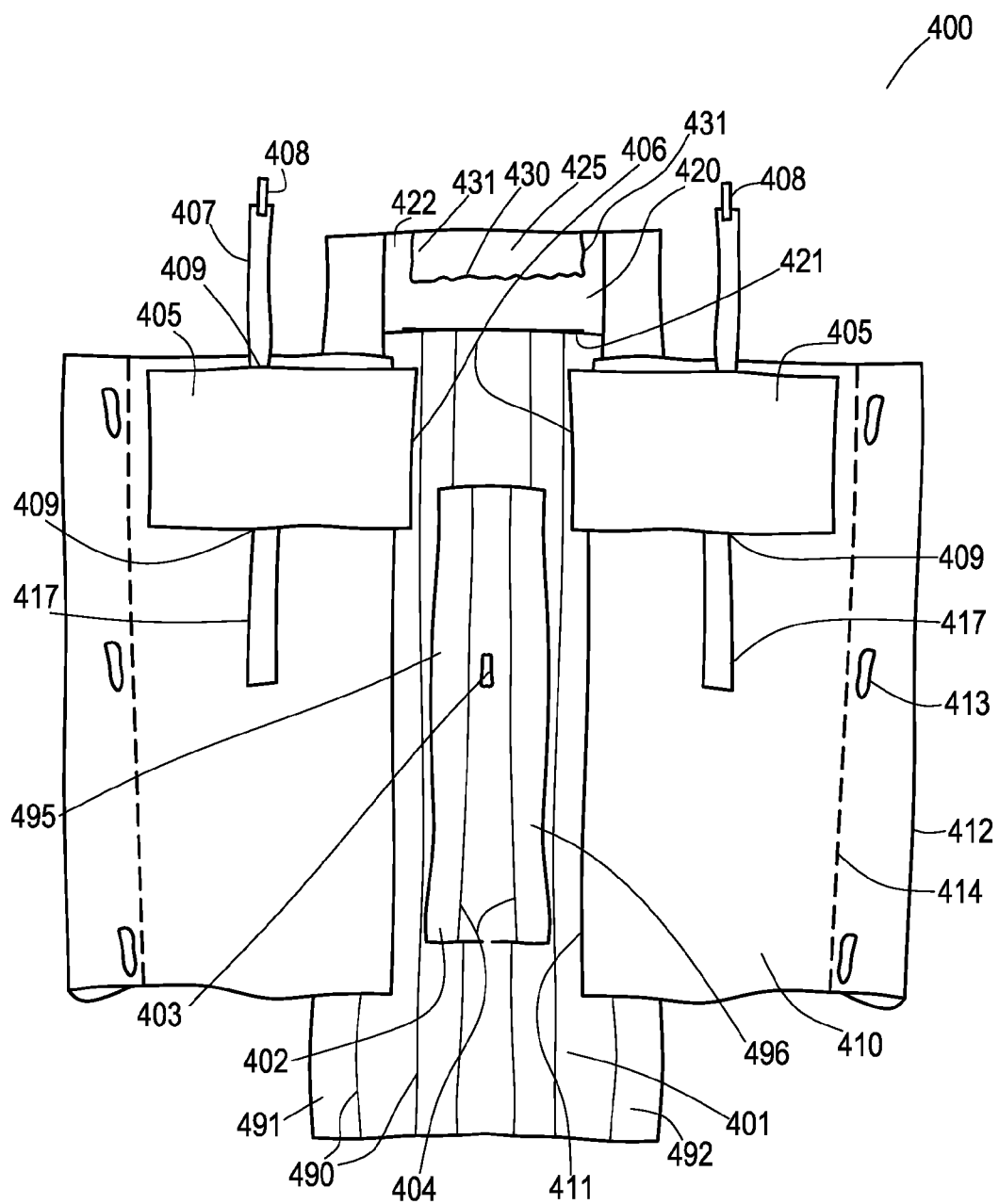
FIG. 11 depicts a top view of an exemplary disposable operating room surgical draping system comprising a one-piece, multi-functional drape of the present invention.

The disposable operating room surgical draping system of the present invention may further comprise one or more panels such as exemplary panels 410 shown in FIG. 11. Typically, panels used in the present invention comprise a single-layer material such as a film layer, a paper layer, or a fabric layer. Desirably, the panels used in the present invention comprise a film material, more desirably, a transparent film material. The film material may comprise any polymeric film-forming material, such as polyethylene, and typically has an average layer thickness of less than about 50 microns (μm) (about 2 mil).

The panels used in the present invention may further comprise a film material having one or more fasteners attached to a surface of the panel. Suitable fasteners include, but are not limited to, hook-and-loop fasteners, and double-sided pressure-sensitive adhesive tapes. Such fasteners may be used to releasably attach a portion of a panel to other surfaces including, but not limited to, a surface of an operating room table sheet, a surface of the panel, or both.

In one desired embodiment of the present invention, the panel comprises a first set of fasteners for attaching an upper edge of the panel to an upper surface of the operating room table sheet. In a further desired embodiment of the present invention, the panel also comprises a second set of fasteners along a lower outer edge of the panel (i.e., an edge of the panel away from the operating room table sheet). The second set of fasteners may be used to releasably fasten the lower outer edge of the panel to a portion of the panel between the lower outer edge and the operating room table sheet so as to shorten an extending distance of the panel (i.e., a distance extending from the operating room table downward toward the floor of the operating room). This features enables the panel(s) for a given disposable operating room surgical draping system to be adjusted for use on a variety of operating room tables having different table heights so that the panels do not extend significantly onto the floor creating a potential safety hazard.

Panels used in the present invention typically have dimensions so that the panel substantially covers an area extending downward from the operating room table to the floor of the operating room, and across a substantial portion of the total length of the operating table. In one exemplary embodiment of the present invention, the panel has a width (i.e., the dimension extending from the operating room table toward the floor) ranging from about 24 inches to about 60 inches, and a length (i.e., the dimension extending along the length of the operating room table sheet) ranging from about 48 inches to about 72 inches. In one desired embodiment, the panel has a width of about 35 inches, and a length of about 61 inches.

Typically, a given disposable operating room surgical draping system of the present invention comprises two panels on either side of an operating room table sheet. In one desired embodiment of the present invention, the disposable operating room surgical draping system of the present invention comprises two substantially identical transparent panels on either side of an operating room table sheet extending from the operating room table sheet to the floor of the operating room.

In yet a further embodiment of the present invention, each panel of the surgical draping system may have a perforated line extending along a length of the panel adjacent to the operating room table sheet (i.e., extending along edges 411 of panels 410 shown in FIG. 11). In this embodiment, if a user does not want to use panels, the user can easily tear the panels along the perforated lines. Alternatively, when a panel is temporarily attached to the operating room table sheet, the panel may be removed from the operating room table sheet by removing the panel via the releasable fastener described above.

F. Pouches

The disposable operating room surgical draping system of the present invention may further comprise one or more pouches for capturing body fluids during a surgical procedure. The one or more pouches may be separate from and/or attached to one or more of the above-described surgical draping system components. In one embodiment of the present invention, pouches are incorporated into the above-described panels such that each pouch extends along a length of each panel (e.g., along a length of panel 410 between edge 411 and edge 414 as shown in FIG. 11). In this embodiment, tubing may be connected to a pouch outlet in order to provide fluid flow out of the pouch and into a separate reservoir.

In other embodiments of the present invention, one or more pouches may be integrated into the above-described operating room table sheet, one or more of the above-described lift sheets, one or more of the above-described arm board covers, one or more of the above-described head covers, or any combination thereof.

Typically, pouches used in the present invention comprise a single or multi-layer materials such as the materials used to make the above-described operating room table sheet, lift sheets, arm board covers, head covers, and panels. Desirably, the pouches used in the present invention comprise a liquid impervious laminate or film material, more desirably, a transparent film material. The film material may comprise any polymeric film-forming material, such as polyethylene, and typically has an average layer thickness of less than about 50 microns (μm) (about 2 mil).

G. Component Additives

Any of the above-described disposable operating room surgical draping system components of the present invention may further comprise one or more additives coated onto or incorporated in one or more of the materials used to form the individual component. Suitable additives include, but are not limited to, antimicrobial agents, colorants, additives to increase the coefficient of friction of a given component layer, etc. In one desired embodiment of the present invention, one or more components of the disposable operating room surgical draping system comprises an antimicrobial agent incorporated therein. Suitable antimicrobial agents include, but are not limited to, triclosan and other antimicrobial agents commercially available under the trade designation MICROBAN®.

II. Disposable Operating Room Surgical Draping System Configurations

The disposable operating room surgical draping system of the present invention may comprise one or more of the above-described components, and be configured to minimize the amount of time and manpower necessary to properly prepare an operating table for use. The components of the disposable operating room surgical draping system of the present invention may be positioned relative to one another, folded into a given configuration, and packaged in such a way as to eliminate the guess work of preparing an operating room setting.

For example, as shown in FIG. 1, exemplary disposable operating room surgical draping system 10 provides the following order of components in the exemplary assembly: operating room table sheet 12 in an unfolded configuration, fan-folded lift sheet 14 positioned next to and over a central portion of operating room table sheet 12, arm board cover 18 (with arm board strap 20 positioned around a portion of arm board cover 18) positioned next to and over a portion of fan-folded lift sheet 14, and head rest cover 16 positioned next to and over a portion of arm board cover 18. With such a configuration, a hospital nurse or other operating room personnel can readily identify and quickly assimilate the various components of the disposable operating room surgical draping system in order to properly cover an operating room table.

Figure 2:
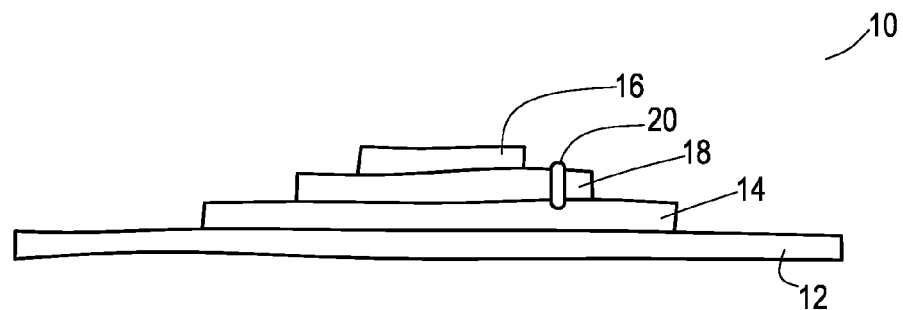
FIG. 2 depicts a side view of the exemplary disposable operating room surgical draping system of FIG. 1 shown along line A-A in FIG. 1.

The stack of disposable operating room surgical draping system components for exemplary disposable operating room surgical draping system 10 may be seen more clearly in FIG. 2, which depicts a side view of the exemplary disposable operating room surgical draping system of FIG. 1 shown along line A-A in FIG. 1. Such a stack of components may be nested and folded with one another as shown in FIGS. 3-7.

Figure 3:
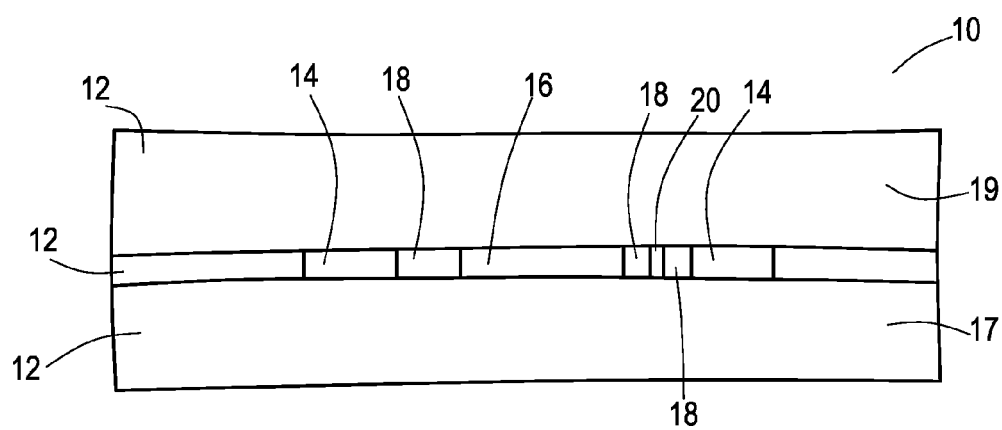
FIG. 3 depicts a top view of the exemplary disposable operating room surgical draping system of FIG. 1 in a folded configuration.

Exemplary disposable operating room surgical draping system 10 of FIG. 1 may be folded along fold lines as shown in operating room table sheet 12 and lift sheet 14. First, lift sheet 14 may be fan folded along fold lines 141 to provide fan-folded lift sheet 14 on operating room table sheet 12. The other components may be assembled as desired prior to folding operating room table sheet 12 along fold lines 15. Operating room table sheet 12 is then fan-folded along fold lines 15 so that outer edge upper surfaces 17 and 19 of fan-folded operating room table sheet 12 are on an upper portion of the folded configuration. FIG. 3 depicts a top view of exemplary disposable operating room surgical draping system 10 of FIG. 1 in the above-described fan-folded configuration.

As shown in FIG. 3, only portions of fan-folded lift sheet 14, arm board cover 18, arm board strap 20, and head rest cover 16 can be seen once operating room table sheet 12 is in a fan-folded configuration. By separating outer edge upper surfaces 17 and 19 of fan-folded operating room table sheet 12 from one another (i.e., pulling outward by grabbing portions of operating room table sheet 12 along outer edge upper surfaces 17 and 19), the fan-folded configuration shown in FIG. 3 converts to the opened configuration as shown in FIG. 1.

Figure 4:
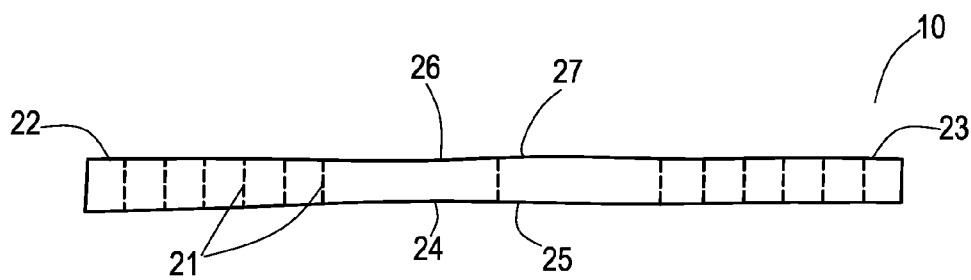
FIG. 4 depicts a side view of the exemplary disposable operating room surgical draping system of FIG. 3 showing exemplary fold lines.
Figure 5:
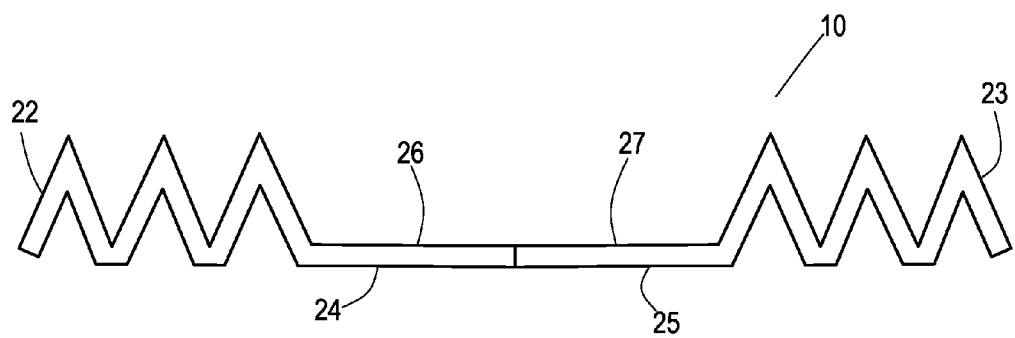
FIG. 5 depicts a side view of the exemplary disposable operating room surgical draping system of FIG. 4 during an exemplary folding operation.
Figure 6:
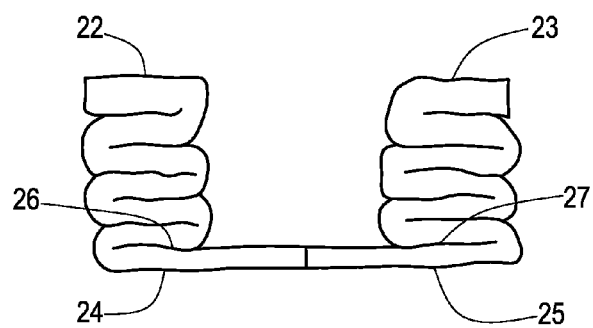
FIG. 6 depicts a side view of the exemplary disposable operating room surgical draping system of FIG. 4 in a folded configuration following an exemplary folding operation.

FIG. 4 provides a side view of exemplary disposable operating room surgical draping system 10 when in a fan-folded configuration as shown in FIG. 3. As shown in FIG. 4, exemplary disposable operating room surgical draping system 10 may be further fan-folded along fold lines 21. Using this exemplary folding procedure, two similar stacks are formed on upper surfaces 26 and 27 such that upper surfaces 22 and 23 are on top of the two similar stacks. This intermediate configuration has upper surfaces 22 and 23, and lower surfaces 24 and 25. FIG. 5 provides a side view of exemplary disposable operating room surgical draping system 10 during the above-described exemplary folding operation. Further, FIG. 6 provides a side view of exemplary disposable operating room surgical draping system 10 in the resulting folded stack intermediate configuration following the above-described exemplary folding operation, wherein the folded stack has upper surfaces 22 and 23, and lower surfaces 24 and 25. As shown in FIG. 6, there is typically a gap of about 1 to 2 inches between the two stacks so that the stacks can be folded a final time as discussed below.

Figure 7:
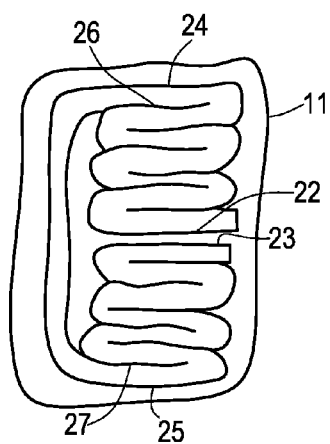
FIG. 7 depicts a side view of an exemplary disposable operating room surgical draping system of FIG. 1 in a folded configuration and encompassed by an optional packaging material.

FIG. 7 depicts a side view of exemplary disposable operating room surgical draping system 10 in a final folded stack configuration and further enclosed by kit lining or packaging material 11. As shown in FIG. 7, exemplary disposable operating room surgical draping system 10 is folded a final time so that upper surfaces 22 and 23 are adjacent to one another, and lower surfaces 24 and 25 form outermost surfaces of the resulting folded configuration. Typically, optional packaging material 11 comprises a disposable, transparent polymeric film material such as polyethylene film. However, any other packaging material may be used in the present invention including, but not limited to, paper packaging materials.

It should be understood that the above-described folding procedure is only an exemplary folding procedure suitable for folding and packaging an exemplary disposable operating room surgical draping system of the present invention. Other folding procedures may be used in the present invention. For example, one alternative folding procedure comprises placing one or more components (e.g., one or more arm board covers, one or more head rest covers, etc.) on top of a lift sheet prior to folding the lift sheet so that the one or more components are nested within the lift sheet, which may further be nested within an operating room table sheet. Such an alternative folding procedure could utilize the exemplary disposable operating room surgical draping system as shown in FIG. 8.

Figure 8:
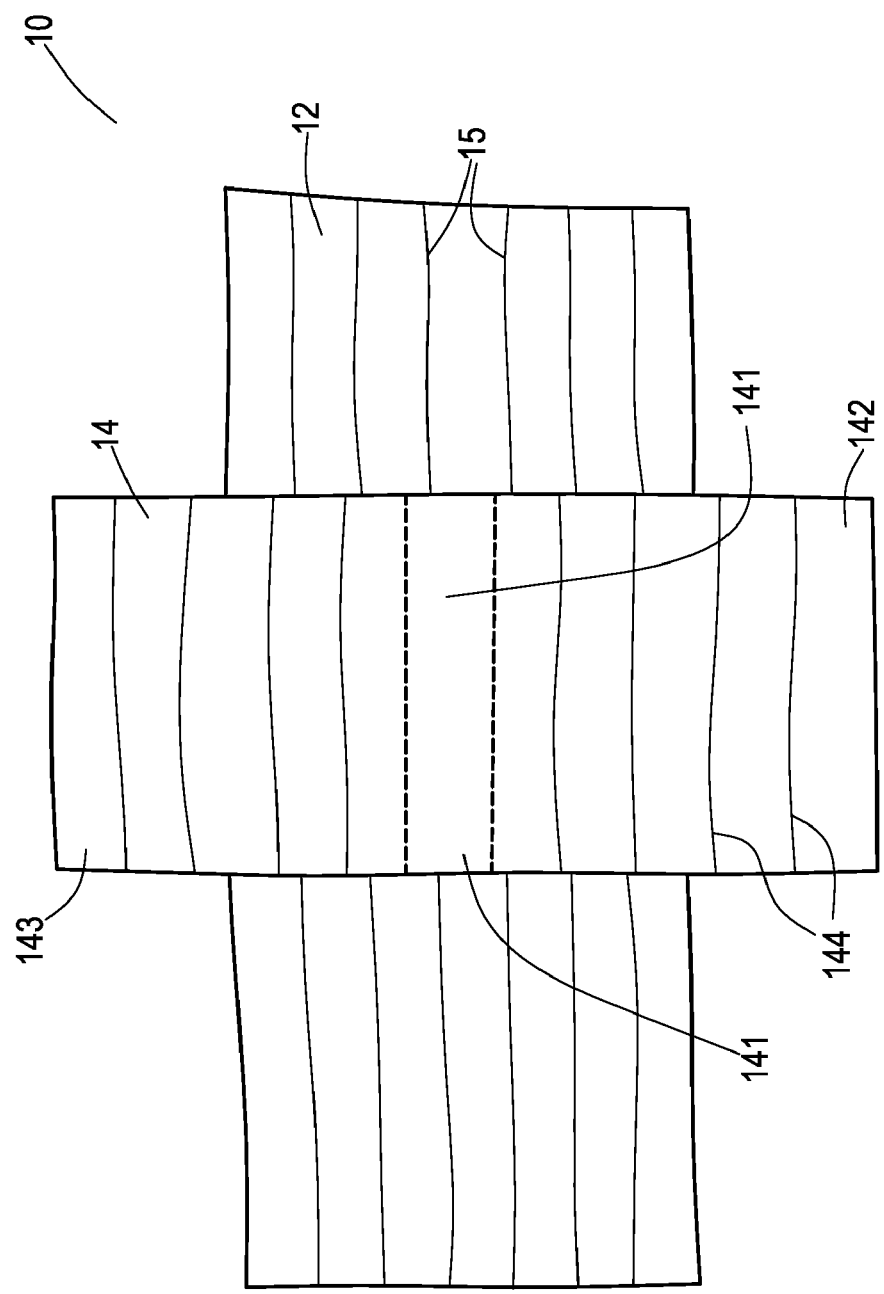
FIG. 8 depicts a top view of the exemplary disposable operating room surgical draping system of FIG. 1 before the lift sheet has been fan folded as shown in FIG. 1.

FIG. 8 depicts a top view of exemplary disposable operating room surgical draping system 10 of FIG. 1 prior to fan-folding lift sheet 14 (as shown in FIG. 1). Expanded lift sheet 14 comprises outer edge upper surfaces 142 and 143 and fold lines 144. When fan-folded, lift sheet 14 and fan-folded operating room table sheet 12 occupy area 121 shown on operating room table sheet 12. As discussed above, one or more nested components (e.g., head rest covers and arm board covers) can be placed on lift sheet 14 in area 121 prior to fan-folding the sheets.

Figure 9:
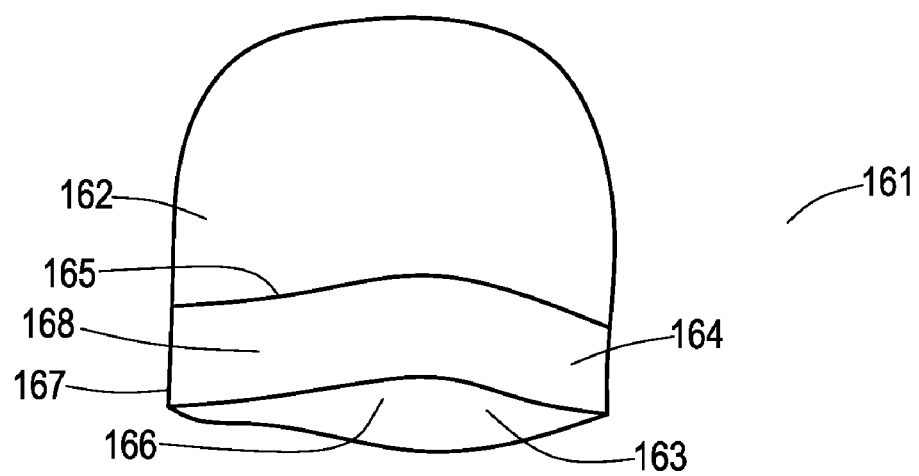
FIG. 9 depicts an exemplary head rest cover suitable for use in the disposable operating room surgical draping system of FIG. 1.
Figure 10:
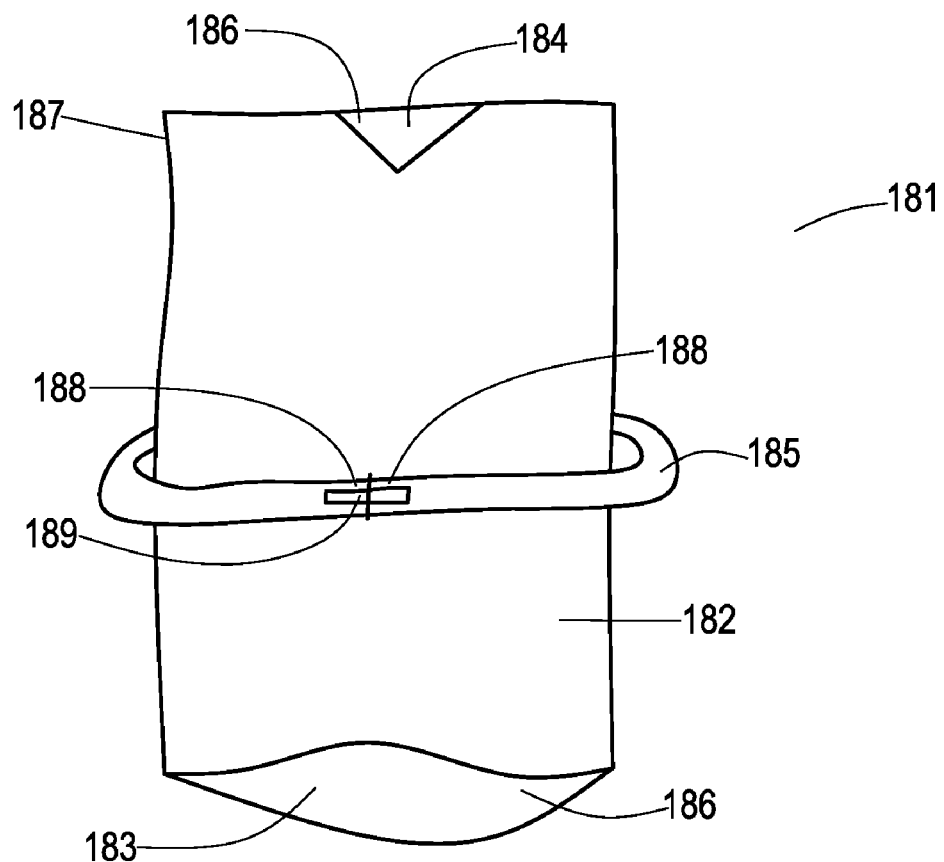
FIG. 10 depicts an exemplary arm board cover suitable for use in the disposable operating room surgical draping system of FIG. 1.

Exemplary head rest covers and arm board covers suitable for use in the disposable operating room surgical draping systems of the present invention are shown respectively in FIGS. 9 and 10. As shown in FIG. 9, exemplary head rest cover 161 comprises a tubular structure having an outer surface 162, and an inner surface 163 within tube cavity 166. As discussed above, desirably, outer surface 162 comprises a fiber-containing material, while inner surface 163 comprises a liquid impervious material. Exemplary head rest cover 161 further comprises cuff 164 located at end 167 of exemplary head rest cover 161. Cuff 164 provides a pocket 165 on exemplary head rest cover 161 so that exemplary head rest cover 161 can be fitted onto a head positioning device as described above. Typically, an inner surface of pocket 165 comprises a fiber-containing material (as described above), while outer surface 168 of cuff 164 comprises a liquid impervious material (as described above).

Exemplary arm board cover 181 shown in FIG. 10 comprises a tubular structure having an outer surface 182, and an inner surface 183 within tube cavity 186. As discussed above, desirably, outer surface 182 comprises a fiber-containing material, while inner surface 183 comprises a liquid impervious material. Exemplary arm board cover 181 further comprises opening 184 located at end 187 of exemplary arm board cover 181. Opening 184 provides communication with tubular cavity 186 of arm board cover. Exemplary strap 185 is also shown in FIG. 10. In this embodiment, exemplary strap 185 comprises a single strap material having strap ends 188, which can be releasably attached to one another using fastener 189. Suitable strap materials and fasteners are described above.

The above-described disposable operating room surgical draping systems of the present invention may include one or more of the following separate components: an optional kit lining or packaging material; one or more arm board covers; one or more head rest covers; one or more arm band straps; one or more panels; an operating room table sheet; one or more lift sheets nested within the operating room table sheet such that when the surgical draping system is unpacked on an operating room table, the lift sheet(s) and operating room table sheet are automatically arranged in the correct order and orientation. According to the teachings of the present invention, operating room personnel can set up an operating room by simply unpacking the surgical draping system. For example, the operating room table sheet may be unfolded and laid down on the operating room table. Next the lift sheet, which is typically fan-folded, is unfolded to provide a lift sheet, which is already nested on top of the operating room table sheet in the appropriate orientation. Similarly, any arm board covers, head rest covers, and arm band straps, which may be nested within the lift sheet or the operating room table sheet are already located in the appropriate location for setting up an operating table.

In a further embodiment of the present invention, one or more of the above-described disposable operating room equipment surgical draping system components may be attached to one another to form a one-piece multi-functional operating room equipment drape or sheet. Like the multi-component assemblies described above, the one-piece multi-functional operating room surgical draping system completely protects the operating room table from exposure to blood and body fluids during use. Further, the one-piece multi-functional operating room surgical draping system covers and protects the horizontal and vertical surfaces of the surgical table, other attachments (i.e., such as arm boards), and areas directly under the operating room table.

In one desired embodiment of the present invention, the disposable operating room surgical draping system comprises an operating room table sheet as described above having one or more of the above-described components attached to the operating room table sheet. One such exemplary disposable operating room surgical draping system is shown in FIG. 11.

As shown in FIG. 11, exemplary disposable operating room surgical draping system 400 comprises operating room table sheet 401 in an unfolded configuration, and having fold lines 490 running lengthwise along operating room table sheet 401. Operating room table sheet 401 further comprises outer edge upper surfaces 491 and 492 running lengthwise along operating room table sheet 401. Fan-folded lift sheet 402 is positioned in a central area of operating room table sheet 401, and attached to operating room table sheet 401 via fastener 403. Fold lines 404 and outer edge upper surfaces 495 and 496 are shown running lengthwise in fan-folded lift sheet 402.

In this embodiment, exemplary operating room table sheet 401 further comprises cuff 425 located on a lower surface of operating room table sheet 401. Cuff 425 provides a pocket along line 430 and outlined by perpendicular lines 431 so that exemplary operating room table sheet 401 can be fitted onto an operating room table mattress as described above. Typically, in this embodiment, an inner surface of the pocket formed by cuff 425 comprises a liquid impervious material (as described above), while an outer surface of cuff 425 (i.e., the lower surface of operating room table sheet 401) comprises a fiber-containing material (as described above).

Exemplary disposable operating room surgical draping system 400 further comprises two arm board covers or "wings" 405 attached to operating room table sheet 401 along lines 406. Desirably, in this embodiment, arm board covers 405 comprise a flat structure, and extend outward from operating room table sheet 401 to cover arm boards (not shown) associated with an operating room table. Each of arm board covers 405 have attached thereto (along edges 409) a set of corresponding straps 407 and 417, which may be releasably attached to one another via fasteners 408. Suitable strap materials and fasteners have been described above. Further, each of arm board covers 405 may comprise one or more fasteners (not shown) along an outer surface of arm board covers 405 so that arm board covers 405 may be repositioned along an outer surface of operating room table sheet 401 as desired.

Exemplary disposable operating room surgical draping system 400 also comprises head rest cover 420 attached to operating room table sheet 401 along line 421. Desirably, in this embodiment, head rest cover 420 comprises a flat structure, and extends upward from operating room table sheet 401 to cover a head positioning device (not shown) associated with an operating room table. End 422 of head rest cover 420 may be used to cover such a head positioning device (see also, FIG. 13).

Exemplary disposable operating room surgical draping system 400 even further comprises panels 410 attached to opposite side of operating room table sheet 401 along edges 411. Desirably, in this embodiment, each of panels 410 comprises a transparent film material, and extends outward from operating room table sheet 401 a distance equal to the distance from the operating room table to the floor of the operating room. As shown in FIG. 11, each of panels 410 comprises a set of fasteners 413 along an outermost edge 414 of panels 410. Fasteners 413 may be releasably attached to portions of panels 410 to shorten the overall extending distance of panels 410. As shown in FIG. 11, the overall extending distance of panels 410 is represented as the distance between lines 411 and edges 412. Although not shown in FIG. 11, as described above, each of panels 410 may further comprise a set of fasteners along edge 411 of panels 410 in order to remove one or more of panels 410 from operating room table sheet 401 as desired.

Figure 12:
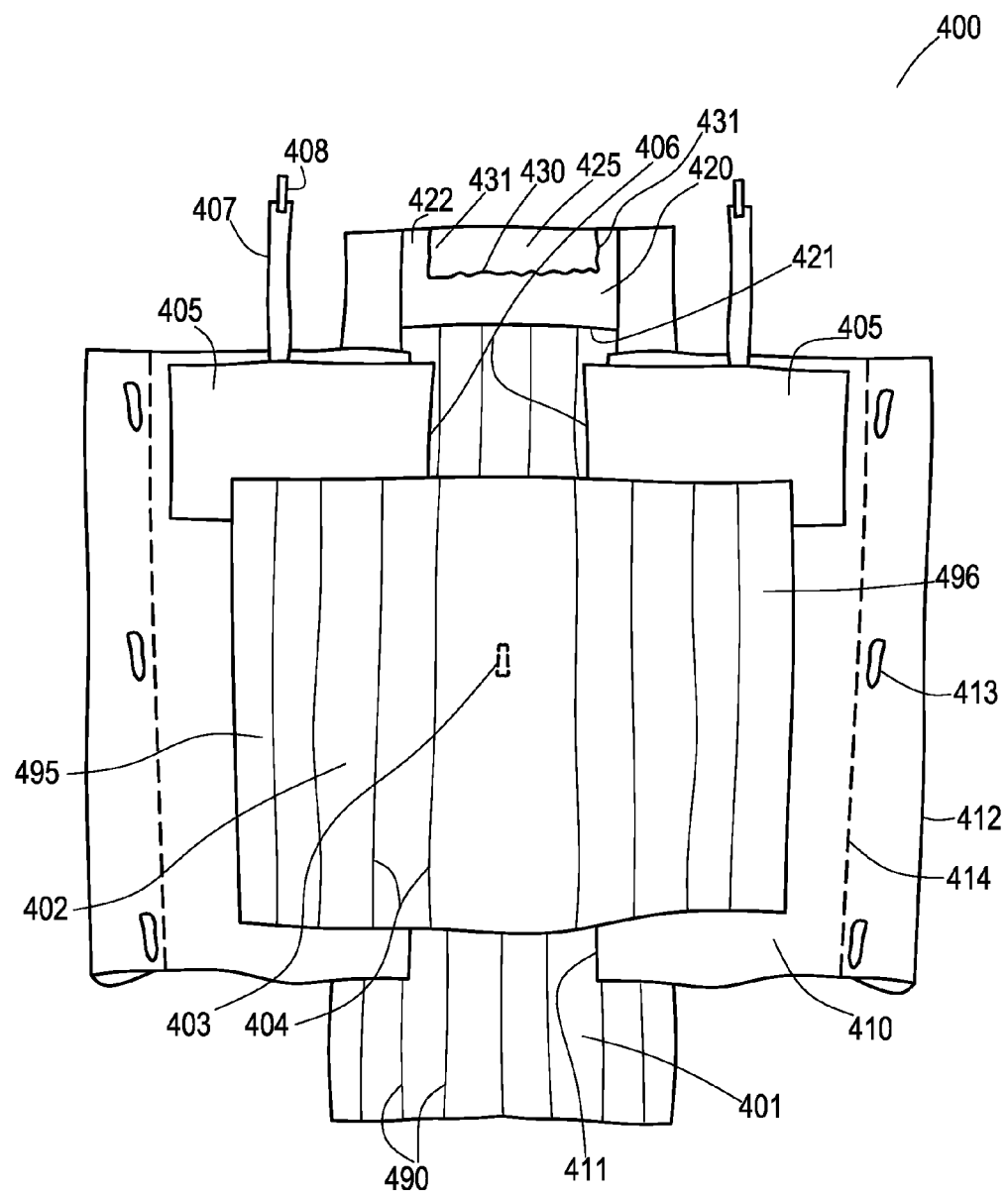
FIG. 12 depicts a top view of the exemplary disposable operating room surgical draping system of FIG. 11 before the lift sheet has been fan-folded as shown in FIG. 11.

Exemplary disposable operating room surgical draping system 400 of FIG. 11 is also shown in FIG. 12 prior to fan-folding lift sheet 402 (as shown in FIG. 11). As shown in FIG. 12, exemplary disposable operating room surgical draping system 400 comprises lift sheet 402 having fold lines 404 therein. As can be seen in FIG. 12, when lift sheet 402 is unfolded, outer edge upper surfaces 495 and 496 of lift sheet 402 are farthest away from operating room table sheet 401.

Figure 13:
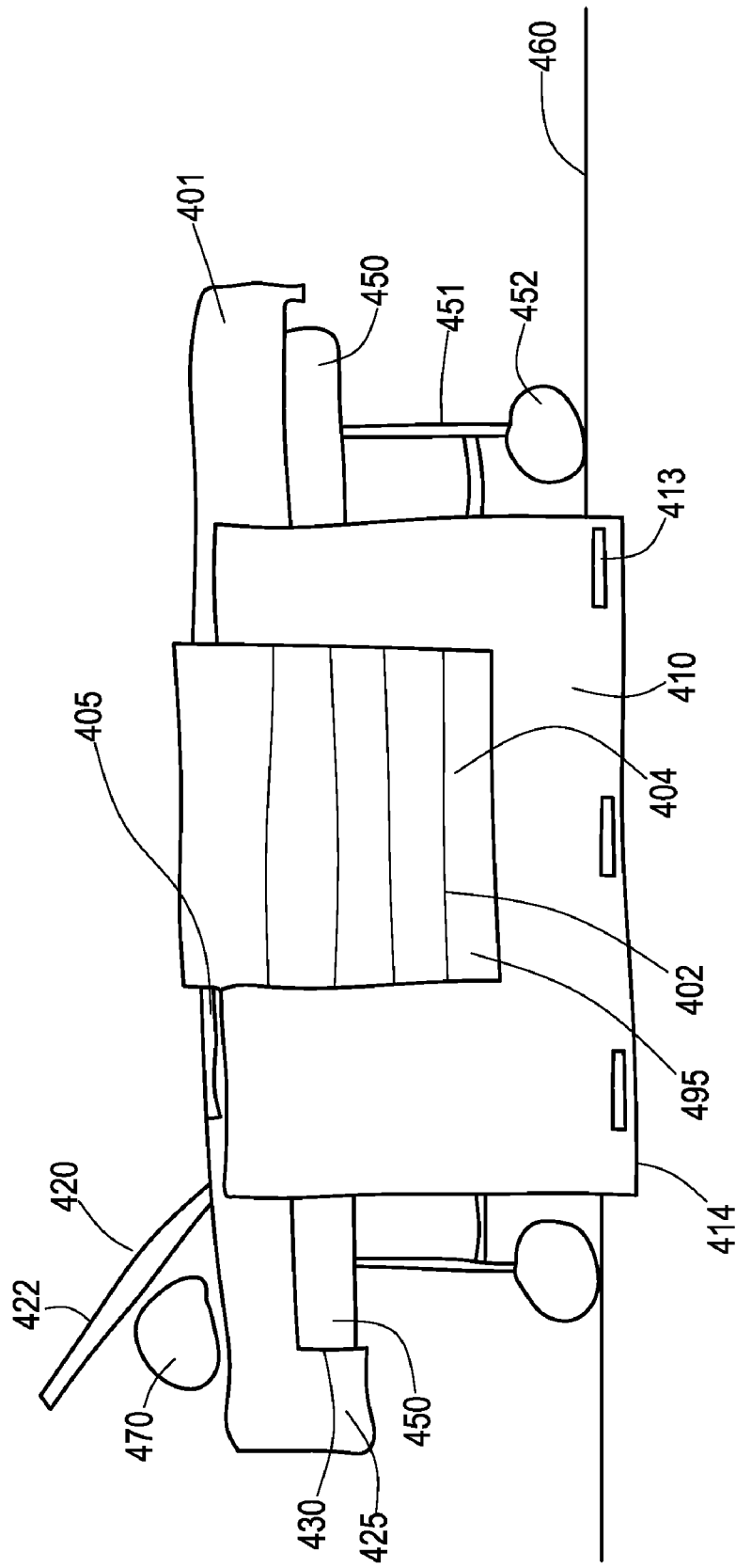
FIG. 13 depicts a side view of an exemplary operating table setting wherein the operating table is covered with the exemplary disposable operating room surgical draping system of FIG. 12.

FIG. 13 depicts a side view of an exemplary operating table setting wherein the operating table is covered with exemplary disposable operating room surgical draping system 400 of FIG. 12. As shown in FIG. 13, exemplary disposable operating room surgical draping system 400 is draped over operating table mattress 450 positioned on operating room table 451 having wheels 452 on operating room floor 460. As can be seen in FIG. 13, operating room table sheet 401 of exemplary disposable operating room surgical draping system 400 extends along and over operating table mattress 450. Cuff 425 of operating room table sheet 401 partially covers (i.e., fits over) operating room table mattress 450 so that a portion of operating room table mattress 450 is within a pocket formed along line 430. Head rest 420 can also be seen positioned over head positioning device 470 such that end 422 of head rest 420 substantially covers head positioning device 470.

As discussed above, panels 410 and lift sheet 402 may be fully extended as shown in FIG. 13. Alternatively, panels 410 may be shortened as described above using fasteners 413 along outermost edge 414 of panel 410. Arm board covers 405 may be positioned over arm boards (not shown) associated with operating room table 451.

In the above-described exemplary disposable operating room surgical draping system 400, each of the above-described components attached to operating room table sheet 401 may be fan-folded independently or simultaneously along with operating room table sheet 401 to form a folded configuration. Such an exemplary folding configuration and method of folding is shown in FIGS. 14-17.

Figure 14:
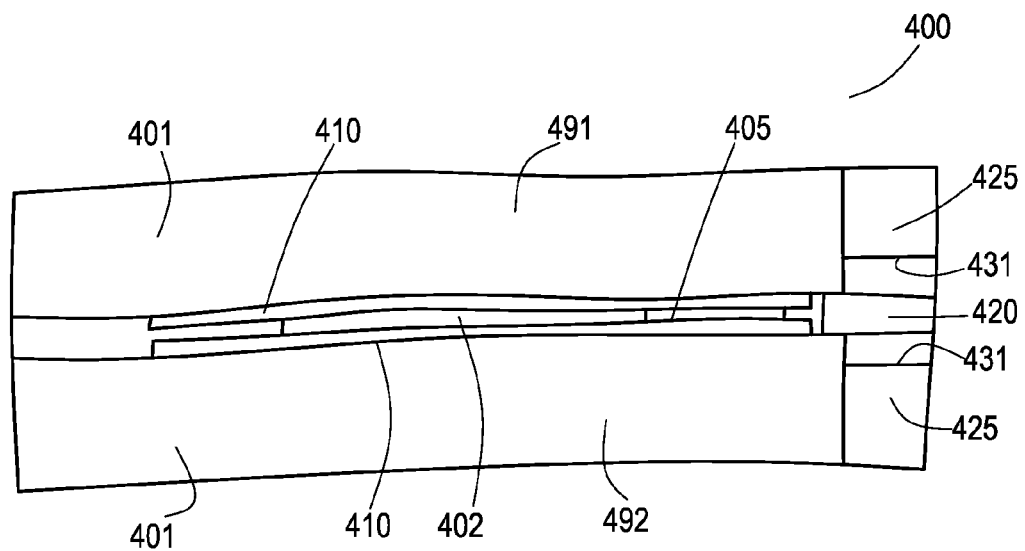
FIG. 14 depicts a top view of the exemplary disposable operating room surgical draping system of FIG. 11 in a folded configuration.

Referring to FIG. 11, exemplary disposable operating room surgical draping system 400 may be folded along fold lines as shown in operating room table sheet 401 and lift sheet 402 (fold lines 490 and 404 respectively). Lift sheet 402, as well as panels 410 and arm board covers 405, may be fan-folded independently along respective fold lines or may be simultaneously fan-folded along with operating room table sheet 401. In either case, operating room table sheet 401 is fan-folded along fold lines 490 so that outer edge upper surfaces 491 and 492 of fan-folded operating room table sheet 401 are on an upper portion of the folded configuration. FIG. 14 depicts a top view of exemplary disposable operating room surgical draping system 400 of FIG. 11 in the above-described fan-folded configuration.

As shown in FIG. 14, only portions of lift sheet 402, arm board covers 405, head rest cover 420, and panels 410 can be seen once operating room table sheet 401 is in a fan-folded configuration. A portion of cuff 425 bound by lines 431 may also be seen when operating room table sheet 401 is in a fan-folded configuration as shown in FIG. 14. By separating outer edge upper surfaces 491 and 492 of fan-folded operating room table sheet 401 from one another (i.e., pulling outward by grabbing portions of operating room table sheet 401 along outer edge upper surfaces 491 and 492), the fan-folded configuration shown in FIG. 14 converts to the opened configuration as shown in FIG. 11.

Figure 15:
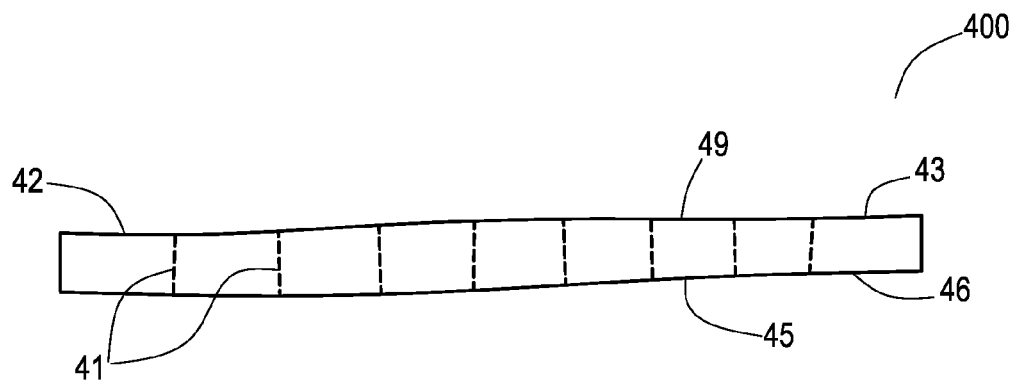
FIG. 15 depicts a side view of the exemplary disposable operating room surgical draping system of FIG. 14 showing exemplary fold lines.
Figure 16:
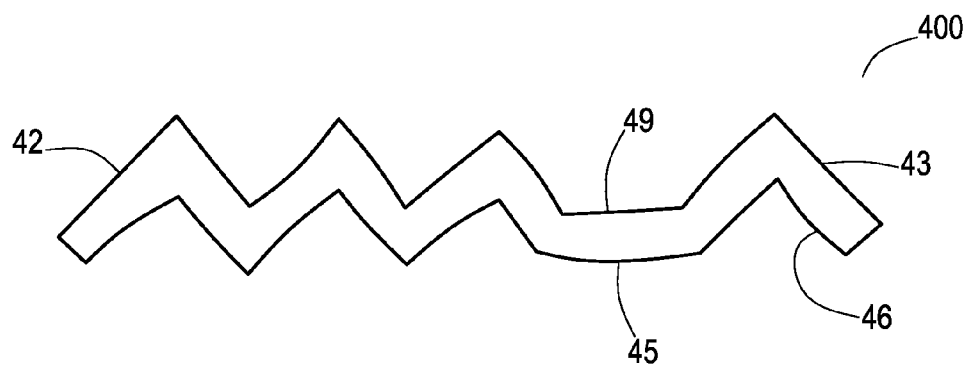
FIG. 16 depicts a side view of the exemplary disposable operating room surgical draping system of FIG. 14 during an exemplary folding operation.

FIG. 15 provides a side view of exemplary disposable operating room surgical draping system 400 when in a fan-folded configuration as shown in FIG. 14. As shown in FIG. 15, exemplary disposable operating room surgical draping system 400 may be further fan-folded along fold lines 41. Using this exemplary folding procedure, a stack is formed on upper surface 49 such that upper surface 42 is on top of the stack. This intermediate configuration has upper surface 22 and lower surface 45. FIG. 16 provides a side view of exemplary disposable operating room surgical draping system 400 during the above-described exemplary folding operation.

Figure 17:
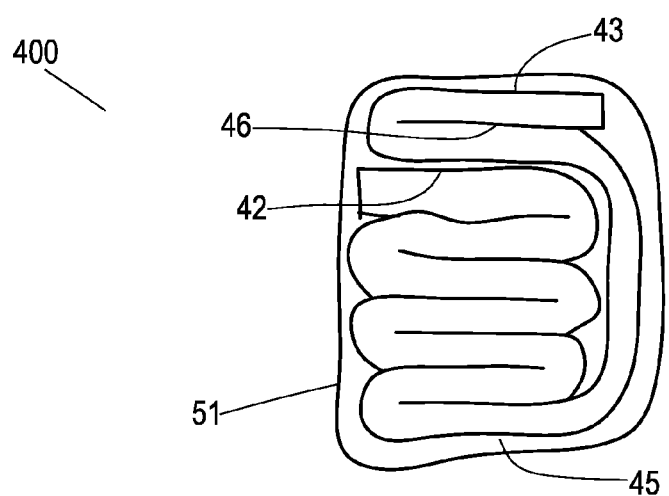
FIG. 17 depicts a side view of an exemplary disposable operating room surgical draping system of FIG. 14 in a folded configuration and encompassed by an optional packaging material.

FIG. 17 provides a side view of exemplary disposable operating room surgical draping system 400 in a final folded stack configuration following the above-described exemplary folding operation, and a final folding step wherein upper surface 43 is folded over upper surface 22. As shown in FIG. 17, in the final folded configuration, uppermost surface 43 is over surface 46, both of which are over previous upper surface 42. In this exemplary folding procedure, lower surface 45 is still the lowermost surface in the final folded stack configuration.

FIG. 17 also depicts exemplary disposable operating room surgical draping system 400 enclosed by optional kit lining or packaging material 51. As discussed above, optional packaging material 51 may comprises any suitable packaging material including, but not limited to, film packaging materials, and paper packaging materials. Desirably, packaging material 51 comprises a disposable, transparent polymeric film material such as polyethylene film.

It should be understood that the above-described folding procedure is only an exemplary folding procedure suitable for folding and packaging an exemplary disposable operating room surgical draping system of the present invention. Other folding procedures may be used in the present invention.

In yet a further desired embodiment of the present invention, the disposable operating room surgical draping system comprises an operating room table sheet, wherein the operating room table sheet has a cuff at one end and on a lower surface of the operating room table sheet as described above. The cuff may be sized so as to be capable of partially enclosing a portion of an operating room table mattress as described above. In this embodiment, one or more of the above-described additional components may be separate from or attached to the cuff-containing operating room table sheet. Desirably, the disposable operating room surgical draping system further comprises a lift sheet attached to the operating room table sheet; two arm board covers attached to the operating room table sheet, each of the arm board covers having strap components attached thereto so that ends of the strap components are releasably attachable to one another; and a head rest cover attached to the operating room table sheet. The disposable operating room surgical draping system may further comprise two separate panels attached to opposite sides of the operating room table sheet, wherein each panel comprises a transparent polymer film and one or more fasteners attached to an outer surface of the panel along an outer edge of the panel away from the operating room table sheet, and wherein each of the fasteners comprises a double-sided, pressure-sensitive adhesive tape which is releasably fastenable to a portion of the panel between the outer edge and the operating room table sheet so as to shorten an extending distance of the panel.

In addition to the above-described disposable operating room surgical draping systems, the present invention is directed to an operating room table in combination with any of the above-described disposable operating room surgical draping systems. Further, the present invention is directed to a packaged disposable operating room surgical draping system comprising any of the above-described disposable operating room surgical draping systems, and a kit lining or packaging material enclosing the disposable operating room surgical draping system.

III. Methods of Preparing an Operating Room Table Using an Disposable Operating Room Surgical Draping System The present invention is further directed to methods of preparing an operating room table using any one of the above-described disposable operating room surgical draping systems. In one exemplary embodiment of the present invention, the method comprises the steps of placing a disposable operating room surgical draping system onto an upper surface of an operating room table; removing a kit lining or packaging material from the disposable operating room surgical draping system if present; and unfolding the disposable operating room surgical draping system. The exemplary method may further comprises one or more of the following steps:

(1) placing at least one head rest cover over a head resting or positioning component;

(2) sliding at least one arm board cover over an arm board of the operating room table, or alternatively, placing at least one arm board cover over an arm board of the operating room table;

(3) unfolding the lift sheet as needed;

(4) unfolding one or more panels as needed to extend the one or more panels a distance toward an operating room floor; and (5) positioning one end of the disposable operating room surgical draping system so that a cuff of the disposable operating room surgical draping system fits over a portion of an operating room table mattress.

The present invention is described above and further illustrated below by way of examples, which are not to be construed in any way as imposing limitations upon the scope of the invention. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Preparation of an Operating Room Surgical Draping System

An exemplary disposable operating room surgical draping system as shown in FIG. 1 was prepared. The following order was used to strategically position the components within the system: (1) an operating room table sheet was provided in an unfolded configuration, (2) a fan-folded lift sheet was positioned next to and over a central portion of the operating room table sheet, (3) two arm board covers with arm board straps positioned around a portion of each arm board cover were positioned on top of one another and next to and over a portion of the fan-folded lift sheet, and (4) a head rest cover was positioned next to and over a portion of the uppermost arm board cover. The system was fan-folded as described in FIGS. 3-7. A label was placed on an upper surface of the surgical draping system to identify the top of the system, and the "head" end (i.e., the end of the system that is to be positioned at the head end of the mattress) of the system.

EXAMPLE 2

Use of an Operating Room Surgical Draping System on an Operating Table

The exemplary disposable operating room surgical draping system of Example 1 was used to prepare an operating room table for surgery. The surgical draping system was placed on an upper surface of an operating room table mattress. The surgical draping system was unfolded with the head end positioned at the head end of the mattress. The operating room table sheet was then unfolded to provide components in the following order: (1) a head rest cover, (2) two arm board covers with straps positioned on top of one another, and (3) a fan-folded lift sheet. The head rest cover and arm board covers were secured to the operating room table, and then the lift sheet was unfolded to complete the preparation.

EXAMPLE 3

Preparation of a One-Piece Surgical Draping System

An exemplary disposable operating room surgical draping system as shown in FIG. 11 was prepared. The following order was used to strategically position the components within the system: (1) an operating room table sheet having a cuff was provided in an unfolded configuration, (2) two panels were adhesively joined to opposite sides of the operating room table sheet, (3) two arm board covers each of which had a set of corresponding straps were adhesively joined to opposite sides of the operating room table sheet toward the cuff end of the operating room table sheet, (4) a lift sheet was adhesively attached to a central portion of the operating room table sheet, (5) the lift sheet was fan-folded, (6) the two arm board covers were fan-folded, (7) the two panels were fan-folded, and (8) the operating room table sheet was fan-folded.

The surgical draping system was further folded as described in FIGS. 14-17. A label was placed on an upper surface of the system to identify the top of the system, and the "head" end (i.e., the end of the system that is to be positioned at the head end of the mattress) of the system.

EXAMPLE 4

Use of a One-Piece Surgical Draping System on an Operating Table

The exemplary disposable operating room surgical draping system of Example 3 was used to prepare an operating room table for surgery. The surgical draping system was placed on an upper surface of an operating room table mattress. The surgical draping system was partially unfolded with the head end positioned at the head end of the mattress. The cuff of the system was fitted over an end of the mattress. The surgical draping system was pulled from an opposite end of the system (i.e., pulled from an upper surface similar to upper surface 42 as shown in FIG. 17) to unfold the surgical draping system to a configuration similar to the configuration shown in FIG. 14.

The operating room table sheet was then unfolded to provide access to the attached components. The head rest cover was positioned over a head positioning device, the panels were unfolded and adjusted in length to extend to the floor of the operating room, the arm board covers were strapped onto arm boards, and the fan-folded lift sheet was unfolded to complete the preparation.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A disposable operating room surgical draping system comprising:
   (a) an operating room table sheet comprising a composite structure comprising:
      (i) a liquid-impervious lower layer;
      (ii) a fiber-containing layer above the liquid impervious layer, said fiber-containing layer comprising a non-woven fabric layer; and
      (iii) at least one layer of superabsorbent material or particles positioned between said liquid-impervious lower layer, and said fiber-containing layer;
   (b) nested draping components in combination with the operating room table sheet, said nested draping components comprising:
      (i) a lift sheet;
      (ii) at least one arm board cover; and
      (iii) at least one head rest cover; and
   (c) one or more room turnover components is selected from bags, disposable wipes, abdominal safety straps, blood solidification systems, suction tubing, and disposable mop heads;
   wherein said operating room table sheet is folded such that the nested draping components are nested within the operating room table sheet.

2. The system of claim 1, wherein the operating room table sheet further comprises a cuff on the lower side of the operating room table sheet, the cuff being sized so as to fit over at least a portion of an operating room table mattress.

3. The system of claim 1, wherein the operating room table sheet is sized such that it completely covers an upper surface of an operating room table mattress.

4. The system of claim 1, wherein the lift sheet further comprises a butterfly lift sheet, wherein said butterfly lift sheet comprises two similarly sized lift sheets tacked to one another along a central portion of the lift sheets running lengthwise along the lift sheets.

5. The system of claim 1, wherein the at least one arm board cover further comprises a strap component.

6. The system of claim 1, wherein the at least one arm board cover comprises at least one tubular arm board cover.

7. The system of claim 1, wherein the at least one tubular arm board cover further comprises a strap component not connected to the tubular arm board cover.

8. The system of claim 1, further comprising two separate panels attached to opposite sides of an upper surface of the operating room table sheet, wherein each panel is capable of extending from an operating room table to an operating room floor positioned beneath the operating room table.

9. The system of claim 1, wherein the operating room table sheet further comprises one or more additives.

10. The system of claim 9, wherein the one or more additive is selected from of antimicrobial agents, colorants, and additives to increase the coefficient of friction of the operating room table sheet.

11. The system of claim 1, wherein at least one of the nested draping components further comprises one or more additives.

12. The system of claim 11, wherein the one or more additive is selected from antimicrobial agents, and colorants.

13. The system of claim 1, wherein the operating room table sheet is fan-folded such that the lift sheet, the at least one arm board cover, and the at least one head rest cover are nested within the fan-folded operating room table sheet.

* * * * *